(12) United States Patent
Badylak et al.

(10) Patent No.: US 6,696,270 B2
(45) Date of Patent: Feb. 24, 2004

(54) GASTRIC SUBMUCOSAL TISSUE AS A NOVEL DIAGNOSTIC TOOL

(75) Inventors: Stephen F. Badylak, West Lafayette, IN (US); George B. Boder, Martinsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/990,906

(22) Filed: Nov. 14, 2001

(65) Prior Publication Data

US 2002/0064807 A1 May 30, 2002

Related U.S. Application Data

(63) Continuation of application No. 09/319,841, filed as application No. PCT/US97/22729 on Dec. 10, 1997, now abandoned.
(60) Provisional application No. 60/032,686, filed on Dec. 10, 1996.

(51) Int. Cl.[7] .............................. C12Q 1/02; C12Q 1/04; C12N 1/20
(52) U.S. Cl. ........................ 435/34; 435/29; 435/256.8; 435/851
(58) Field of Search .................... 435/29, 34, 256.8, 435/851

(56) References Cited

U.S. PATENT DOCUMENTS

| | | | |
|---|---|---|---|
| 4,743,552 A | | 5/1988 | Friedman et al. |
| 4,829,000 A | | 5/1989 | Kleinman et al. |
| 4,902,508 A | | 2/1990 | Badylak et al. |
| 5,275,826 A | | 1/1994 | Badylak et al. |
| 5,281,422 A | | 1/1994 | Badylak et al. |
| 5,478,739 A | | 12/1995 | Slivka et al. |
| 5,518,915 A | | 5/1996 | Naughton et al. |
| 5,554,389 A | | 9/1996 | Badylak et al. |
| 5,866,414 A | * | 2/1999 | Badylak et al. |
| 5,929,299 A | * | 7/1999 | Ikeda et al. |

FOREIGN PATENT DOCUMENTS

WO    WO 96/24661    8/1996

OTHER PUBLICATIONS

Resenberg et al. Scand. J. Gastroenterol. 1991. 26, 43–48.*
Atlas R. Handbook of Microbiologcal Media. 1994. p. 381.*

Badylak S.I., Boder G.B., Morff R., Lantz G., *Directed Connective Tissue Remodeling Upon a Biologic Collagen Substrate*. J. Cell Biochem. Supplement 16F, p. 124, 1992.

Kuo C.Y., Burghen G.A., and Herrod H.G., *Biohybrid Islet–Gland Equivalent for Transplantation*. Journal of Cellular Biochemistry, Supplement 18C, PZ110, Feb. 13–26, 1994.

Kleinman H.K., McGarvey M.L., Hassell J.R., Star V.L., Cannon F.B., Laurie G.W., and Martin G.R. *Basement Membrane Complexes with Biological Activity*, Biochemistry 25:312–318, 1986.

Freshney R.I. *Cultures of Animal Cells: A Manual of Basic Technique*. Chapters 12 and 13, pp. 155–185. Alan R. Liss, Inc.,New York, 1994.

Ibrahiem, E.H.I., et al., Orthotopic Implantation of Primary N–[4–(5–Nitro–2–furyl)–2–thiazoiyl]formamide–induced Bladder Cancer in Bladder Submucosa: An Animal Model for Bladder Cancer Study, Cancer Research, vol. 43:617–620, Feb. 1983.

Demain, et al., *Manual of Industrial Microbiology and Biotechnology*, Washington, D.C.; American Society for Microbiology, 1986, Chapter 20, pp. 248–262.

Kashtan, H. et al., Intra–rectal injection of tumour cells: a novel animal model of rectal cancer, Surgical Oncology, 1:251–256, 1992.

Sigma 1994 Catalogue and Price List, Plant Cell Culture Equipment, p. 160.

Meyer–Rosberg, K. and T. Berglindh, *Scandinavian Journal of Gastroenterology*, vol. 31, No. 5, pp. 434–441 (1996).

Merriam Webster's Collegiate Dictionary, 10th Edition, p. 597 (1993).

* cited by examiner

Primary Examiner—Sandra E. Saucier
Assistant Examiner—Vera Afremova
(74) Attorney, Agent, or Firm—Barnes & Thornburg

(57) ABSTRACT

A cell culture growth substrate comprising submucosal tissue of a warm-blooded vertebrate and a method for culturing fastidious organisms is described. Submucosal tissue used in accordance with the present invention supports the proliferation of cells when said cells are contacted with submucosal tissue under conditions conducive to cell proliferation.

3 Claims, No Drawings

GASTRIC SUBMUCOSAL TISSUE AS A NOVEL DIAGNOSTIC TOOL

CROSS REFERENCE TO RELATED APPLICATIONS

This application is a continuation of U.S. application Ser. No. 09/319,841 filed Jun. 10, 1999 now abandoned, which is a U.S. national application of international application Ser. No. PCT/US97/22729 filed Dec. 10, 1997, which claims priority to U.S. provisional application Ser. No. 60/032,686 filed Dec. 10, 1996.

FIELD OF THE INVENTION

The present invention relates to a submucosal tissue composition and the use of those compositions to promote growth of fastidious cells. More particularly, the present invention is directed to the use of submucosal tissue cell culture substrates to enhance the in vitro growth, and thus the identification and diagnosis, of vertebrate infections agents.

BACKGROUND OF THE INVENTION

Bacteria are a diverse group of organisms that live in a broad variety of environments. In particular, many bacterial species live both on and in vertebrate hosts. Bacteria that colonize the interior spaces of vertebrates typically exhibit specific interactions with the tissues that comprise the bacteria's optimal habitat in the host organism. Many bacteria express adhesions having fine tuned specificities for interacting with eukaryotic cell-surface proteins or carbohydrate structures so that only a restricted range of hosts and tissue that carry the appropriate receptors are available for bacterial colonization.

For example if bacteria cannot adhere to the mucosal layer of the vertebrate digestive system they will be removed rapidly by the local non-specific host-defense mechanisms (peristalsis, ciliary action and turnover of the epithelial cell populations and mucus layer). In addition, competition between bacteria for space and nutrients, and bacteria tolerance of biochemical parameters such as pH and antimicrobial peptides, select for bacterial species/strains that can colonize specific niches. The result of this selective process is often referred to as tissue tropism.

New strains of bacteria are continually being discovered as techniques for their detection improve. However, many detected strains have proven to be difficult to culture outside their natural micronenvironment due to the unique culture conditions required by these organisms. Accordingly, researchers attempting to culture microorganisms try to provide an in vitro microenvironment which mimics the in vivo environment in which the microorganisms grow. The ability to propagate microorganisms in vitro is of particular importance for the identification of infectious and pathogenic organisms, and for diagnosis of diseases. In addition, an in vitro microenvironment which mimics the in vivo environment enables the study of such organisms in vitro.

Many infectious agents when placed on existing culture media often fail to grow and therefore are not detected, given the state of the present technology. One medically significant organism that has proven difficult to culture in vitro is *Helicobacter pylori*, a gram negative spiral shaped microaerophilic bacteria. *H. pylori* live in the mucous layer lining the stomach of vertebrate species and are partially protected from the stomach's acid by the mucosal layer. The organisms secrete proteins that interact with the stomach's epithelial cells and attract phagocytic cells, such as macrophages and leukocytes, and those phagocytic cells induce inflammation and gastritis. In addition, the bacteria produce urease, an enzyme that helps to break down urea into ammonia and carbon dioxide. Ammonia can neutralize stomach acid allowing further proliferation of *H. pylori*. *H. pylori* also secretes toxins that contribute to the formation of stomach ulcers. *H. pylori* has been suggested to be a causative agent of chronic active gastritis and gastric duodenal ulcers. More recently, *H. pylori* infections have also been associated with the development of gastric adenocarcinoma and mucosa-associated lymphoid tissue lymphoma of the stomach.

Many bacteria cannot survive in an acidic environment, however *H. pylori* are not the only bacteria capable of colonizing the surface of a primate's stomach. Since the discovery of *H. pylori* bacteria, scientists have isolated 11 other organisms from the stomachs of other primates such as dog, cats, rodents, ferrets and even cheetahs. These bacteria, for now are considered to be members of the Helocobacter family. All are spiral shaped and highly mobile, properties that enable them to resist muscle contractions that regularly empty the stomach. These organisms grow best at oxygen levels of 5%, matching the level found in the stomachs mucus layer (ambient air is 21% oxygen).

Surveys using an antibody-based blood test to reveal the presence *H. pylori* have indicated that one-third to one-half of the world's population carry *H. pylori*. In the United States and Western Europe children rarely become infected, but the bacteria's prevalence rises with age such that more than half of all sixty year olds in those countries have the bacteria. In contrast, sixty to seventy percent of the children in developing countries show positive test results by age 10, and the infection rate remains higher for adults. *H. pylori* infection is also common in institutionalized children. *H. pylori* is capable of long term persistence in untreated individuals, and in the absence of treatment *H. pylori* remains persistent in the gastric mucosa for the lifetime of the host.

Although blood tests are useful for an initial screen for detecting the existence of an *H. pylori* infection, The blood test is based on detecting antibodies to *H. pylori* and thus is not a direct test for the presence of viable *H. pylori* bacteria. Screening for antibodies only provides information on whether the individual has been exposed to *H. pylori*. Furthermore, the blood test is know to give false positives. The present invention describes a direct assay for the presence of *H. pylori* that utilizes a unique cell culture matrix to grow *H. pylori*.

In 1983 *H. pylori* were cultured in vitro for the first time by using a complex media (Walkers media) and extending the culture timeperiods (5 days instead of the normal 2 day culture). This remains the current method for growing *H. pylori*, and accordingly, the method suffers the disadvantage of requiring long incubation times and the use of expensive complex media formulations. Furthermore, the presently used culture media fail to mimic the natural in vivo environment of *H. pylori*. Cellular morphology and metabolic activity of cultured cells are affected by the composition of the substrate on which they are grown. Presumably cultured cells function best (i.e. proliferate and perform their natural in vivo functions) when cultured on substrates that closely mimic their natural environment. Therefore, current studies of cellular function that are based on the in vitro growth of *H. pylori*, are limited by the lack of cell growth substrates that present the appropriate physiological environment for proliferation and development of the cultured cells. The compositions of the present invention provide a more appropriate physiological growth environment than is currently available for growing cells that naturally occupy the stomachs of vertebrate species.

SUMMARY OF THE INVENTION

The present invention is directed to an extracellular matrix, comprising vertebrate submucosal tissues, that provides the necessary microenvironment to allow the in vitro culture of fastidious organisms. Naturally occurring extracellular matrices have the ability to serve as a substrate for the growth of prokaryotic organisms, fungal agents and less well defined infectious agents of different genus and species which are difficult to grow in standard culture media. The extracellular matrixes of the present invention enhance the growth, and thus the detection of, and diagnosis of disease states caused by, these organisms. Likewise, cell culture substrates comprising submucosal tissue isolated from the stomach, the urinary tract, or the intestines can be utilized to mimic the natural in vivo environments of those tissue source organs. Thus cells growing on such substrates in vitro will provide more physiologically relevant data regarding the susceptibility of these organisms to various potential therapeutic agents.

DETAILED DESCRIPTION OF THE INVENTION

Definitions:

The term "contacting" as used herein with reference to cell culture is intended to include both direct and indirect contact, for example in fluid communication, between the submucosal tissue and the cultured cells.

The term "conditions conducive to fastidious cell growth" and "conditions conducive to prokaryote cell growth" as used herein refer to the environmental conditions, such as sterile technique, temperature and nutrient supply, that are considered optimal for the growth of those cells. Typically those conditions will mimic the conditions the cells are exposed to in their natural habitats.

The term "fastidious organism" or "fastidious cell" as used herein refers to organisms or cells that fail to grow (or grow very slowly) on standard growth substrates. In particular, fastidious organisms include prokaryotes, fungal agents and less well defined infectious agents of different genus and species which are difficult to grow in standard culture media.

There is provided in accordance with this invention a method and composition for supporting the proliferation, in vitro, of fastidious organisms. Generally the method comprises the step of contacting the fastidious cells, in vitro, with a vertebrate submucosa-derived matrix under conditions conducive to the growth of those cells.

The submucosa derived matrices for use in accordance with the present invention comprise highly conserved collagens, glycoproteins, proteoglycans, and glycosaminoglycans in their natural configuration and natural concentration. The submucosal tissue for use in this invention can be obtained from various organ sources, including stomach, bladder or intestinal tissue harvested from animals raised for meat production, including, for example, pigs, cattle and sheep or other warm-blooded vertebrates. This tissue is normally a discarded by-product of meat processing. The tissue can be used in either its natural configuration or in a comminuted or partially digested fluidized form. Vertebrate submucosal tissue is a plentiful by-product of commercial meat production operations and is thus a low cost cell growth substrate, especially when the submucosal tissue is used in its native sheet configuration.

In general submucosal tissue is prepared from warm-blooded tissues including the alimentary, respiratory, intestinal, urinary or genital tracts by delaminating the submucosa from both the smooth muscle layers and the mucosal layers. The preparation of intestinal submucosa is described and claimed in U.S. Pat. No. 4,902,508, the disclosure of which is expressly incorporated herein by reference. Urinary bladder submucosa and its preparation is described in U.S. Pat. No. 5,554,389, the disclosure of which is expressly incorporated herein by reference. Stomach submucosa has also been obtained and characterized using similar tissue processing techniques.

In accordance with one embodiment, the cell culture substrates comprise stomach submucosa derived from stomach tissue of a warm-blooded vertebrate. The wall of the stomach is composed of the following layers: the tunica mucosa (including an epithelium layer, a tunica propria layer consisting of reticular or fine areolar tissue, and a glandular layer), the tunica submucosa layer (composed of areolar tissue and lacking glands), the tunica muscularis layer (composed of three layers of muscle), and the serosa (a layer of mesothelium outside the loose connective tissue which invests the muscle layers). Blood vessels, lymphatic tissue and neurological tissue also pervade the stomach tissues including the tunica submucosa.

Stomach submucosal tissue in accordance with the present invention comprises stomach submucosa delaminated from the glandular portion of the tunica mucosa and the smooth muscle layers of the muscularis externa. The composition has proven to have the ability to induce cell growth and proliferation in vitro, when used as a growth substrate material. In particular a cell substrate comprising stomach submucosal tissue has been found to enhance the in vitro growth of organisms that naturally inhabit the stomach of primates. Furthermore the material can serve as a useful tool for evaluating the natural patterns of growth and proliferation of culture of pathogenic organisms thus allowing better characterization of the pathogenesis of the disease process.

The submucosal cell culture substrates in accordance with one embodiment of the present invention comprises stomach submucosa of a warm-blooded vertebrate delaminated from adjacent stomach tissue layers. In one embodiment the stomach submucosa is prepared from the stomach tissue of primates or other acid producing tissues of vertebrate digestive tracts.

In accordance with one embodiment, the present submucosal cell culture substrates comprise submucosa delaminated from the smooth muscle layers of the muscularis externa and at least the luminal portion of the mucosal layer of a segment of the stomach of a warm-blooded vertebrate. In one embodiment, the submucosal tissue compositions comprise the tunica submucosa and basilar portions of the tunica mucosa of the stomach of a warm blooded vertebrate. Typically the delamination technique described below provides a tissue composition consisting essentially of stomach submucosa. Those compositions are referred to herein generically as stomach submucosal tissue.

The preparation of stomach submucosal tissue from a segment of stomach is similar to the procedure for preparing intestinal submucosal tissue as detailed in U.S. Pat. No. 4,902,508, the disclosure of which is expressly incorporated herein by reference. A segment of stomach tissue is first subjected to abrasion using a longitudinal wiping motion to remove the outer layers (particularly the smooth muscle layers) and the luminal portions of the tunica mucosa layers. The resulting submucosa tissue has a thickness of about 100 to about 200 micrometers, and consists primarily (greater than 98%) of acellular, eosinophilic staining (H&E stain) extracellular matrix material. Occasional blood vessels and spindle cells consistent with fibrocytes are scattered randomly throughout the tissue. Typically the submucosa is rinsed with water for approximately 2 hours and optionally stored in a frozen hydrated state until used as described below.

Fluidized submucosal tissue can be prepared in a manner similar to the preparation of fluidized intestinal submucosa, as described in U.S. Pat. No. 5,275,826 the disclosure of which is expressly incorporated herein by reference. The submucosal tissue is comminuted by tearing, cutting, grinding, shearing and the like. Grinding the submucosal tissue in a frozen or freeze-dried state is preferred although good results can be obtained as well by subjecting a suspension of submucosal tissue pieces to treatment in a high speed (high shear) blender and dewatering by centrifuging and decanting excess water. Additionally, the comminuted fluidized tissue can be solubilized by enzymatic digestion of the submucosal tissue including the use of proteases, such as trypsin or pepsin, or other appropriate enzymes or mixtures of enzymes, for a period of time sufficient to solubilize said tissue and form a substantially uniform or homogeneous solution.

The present invention also contemplates the use of powder forms of submucosal tissue. In one embodiment a powder form of submucosal tissue is prepared by pulverizing submucosal tissue under liquid nitrogen to produce particles ranging in size from 0.1 to 1 mm$^2$. The particulate composition is then lyophilized overnight and sterilized to form a solid substantially anhydrous particulate composite. Alternatively, a powder form of submucosal tissue can be formed from fluidized submucosa by drying the suspensions or solutions of comminuted and/or partially digested stomach submucosa.

The present submucosal tissue compositions may be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the graft is preferably used. For instance, it is believed that strong gamma radiation may cause loss of strength in the graft material. Because one of the most attractive features of the submucosa grafts is their ability to induce host-remodeling responses, it is desirable not to use a sterilization approach which will detract from that property. Preferred sterilization techniques include exposing the graft to peracetic acid, low dose gamma irradiation ($\leq 2.5$ mRad) and gas plasma sterilization; peracetic acid sterilization being the most preferred method. Typically, after the tissue graft composition has been sterilized, the composition is wrapped in a non-porous plastic wrap and sterilized again using ethylene oxide or gamma irradiation sterilization techniques.

The submucosal tissue compositions of the present invention are used in accordance with this invention in a method and composition for promoting the growth and proliferation of fastidious cell cultured in vitro. Generally the method comprises the step of contacting fastidious cells, in vitro, with a vertebrate submucosa-derived matrix under conditions conducive to cell growth. Although optimum cell culture conditions used for culturing cells, such as prokaryotes, depend somewhat on the particular cell type, cell growth conditions are generally well known in the art.

Stomach submucosal tissue of warm blooded vertebrates is one preferred source of the cell culture substrate for use in this invention. Applicants have discovered that compositions comprising stomach submucosal tissue can be used for supporting growth or proliferation of fastidious prokaryotic cells in vitro. Stomach submucosal tissue can be used in accordance with this invention as a cell growth substrate in a variety of forms, including its native sheet-like configuration, as a gel matrix, as a supplemental component in art-recognized cell/tissue culture media, or as coating for cultureware to provide a more physiologically relevant substrate that supports and enhances the proliferation of cells in contact with the submucosal matrix. The submucosal tissue is preferably sterilized prior to use in cell culture applications.

In one preferred embodiment fastidious prokaryotic cells, such as H. pylori, are seeded directly onto sheets of vertebrate stomach submucosal tissue under conditions conducive to prokaryotic cell proliferation. The porous nature of stomach submucosal tissue allows diffusion of cell nutrients throughout the submucosal matrix. Thus, for example, cells can be cultured on either the luminal or abluminal surface of the stomach submucosal tissue. The luminal surface is the submucosal surface facing the lumen of the organ source and typically adjacent to an inner mucosa layer in vivo whereas the abluminal surface is the submucosal surface facing away from the lumen of the organ and typically in contact with smooth muscle tissue in vivo.

To analyzing in vitro the effect of varying cell growth conditions on the growth characteristics of the cultured cells, the cells are seeded on a cell growth substrate comprising stomach submucosal tissue of a warm-blooded vertebrate and provided a culture medium containing nutrients necessary to the proliferation of said cells. The seeded cells are then cultured under a preselected variable cell growth condition for varying lengths of time and then the mucosal tissue substrate and the cell population on the substrate are histologically examined. The selected growth condition can be the presence or concentration of a cell growth modifier compound, such as cytokines or cytotoxic agents, in the nutrient medium. Alternatively, the selected growth condition may be the modification of environmental factors such as temperature, pH, electromagnetic radiation, or nutrient composition. The effect of the selected growth condition on the morphology and growth of the cells can then be assessed by histological analysis of the control (cells cultured in the absence of the selected growth condition) and the test cell cultures.

In another embodiment of the present invention, cell growth substrates in accordance with the present invention are formed from fluidized forms of submucosal tissue that have been solubilized by enzymatic digestion. The fluidized, digested submucosal tissue can be gelled to form a solid or semi-solid matrix, for example, stomach submucosal tissue can be fluidized, enzymatically digested and gelled to form a gelled cell culture substrate comprising stomach submucosal tissue. The viscosity of fluidized submucosa for use in accordance with this invention can be manipulated by controlling the concentration of the submucosa component and the degree of hydration. The viscosity can be adjusted to a range of about 2 to about 300,000 cps at 25° C. Higher viscosity formulations, for example, gels, can be prepared from the submucosa digest solutions by adjusting the pH of such solutions to about 6.0 to about 7.4. Eukaryotic or prokaryotic cells can then be seeded directly on the surface of the matrix and cultured under conditions conducive to cell proliferation.

The cell growth substrate of the present invention can be combined with nutrients, including minerals, amino acids, sugars, peptides, proteins, or glycoproteins that facilitate cellular proliferation. In one preferred embodiment fluidized or powder forms of submucosal tissue can be used to supplement standard culture media to enhance the standard media's capacity for sustaining and inducing the proliferation of fastidious cells cultured in vitro.

In accordance with the present invention there is provided a cell culture composition for supporting growth, in vitro, of fastidious organisms (including both eukaryotic and prokaryotic organisms), the composition comprising submucosal tissue of a warm-blooded vertebrate. The composition may further comprise added nutrients, and/or growth factors required for optimal growth of the cultured cells. The submucosa substrates of the present invention can be used with commercially available cell culture liquid media (both serum based and serum free). When grown in accordance with this invention, proliferating cells can either be in direct contact with the submucosal tissue or they can simply be in fluid communication with the submucosal tissue.

EXAMPLE 1

Preparation of Stomach Submucosal Tissue

The tissue graft material of this invention is prepared in accordance with the following steps:

The stomach is first removed from the animal source by cutting the esophagus and small intestine at their respective entrance and exit points on the stomach. Any excess mesentery tissue or fat is removed from the stomach and the contents of the stomach are emptied and any remaining residues are removed from the inside of the stomach by rinsing with running tap water.

The stomach is then everted to expose the inside layers of the stomach. The portions of the stomach that begin to form the entrance or exit points of the stomach are removed. The stomach is typically left whole, however the stomach can also be cut and flattened prior to removal of unwanted tissues. The luminal surface of the stomach is subject to abrasion using the handle portion of a pair of scissors or hemostats to scrape off the inner layers of the stomach including at least the luminal portion of the tunica mucosa. A thin residual layer will remain at this point. If the tissue was left whole, the stomach tissue is everted again to return the luminal surface of the stomach to the interior of the graft construct. A small cut is then made in the exterior muscle fiber layer. The muscle layers are then delaminated from the submucosal tissue through the use of a pair of scissors or hemostat to enlarge the cut in the muscle and scrape off the muscle layers.

The remaining tissue is everted again to place the luminal side on the exterior of the tissue graft. The luminal surface is scraped to remove the remaining inside residue which has a brownish color. The stomach tissue is scraped until the tissue appears pinkish-white in color. During the preparation of the stomach tissue care is taken to keep the tissue by periodically hydrating the tissue with water. The stomach submucosa tissue is rinsed in running tap water for approximately two hours to remove any blood or loose tissue scrapings. After rinsing the tissue should appear white, if the tissue remains pinkish in color the tissue is rubbed under water until the tissue appears white. After rinsing is complete excess water is removed by ringing the tissue by hand or the use of mechanical ringers. The tissue is then stored in liquid nitrogen at −80° C°.

EXAMPLE 2

In-Vitro Cell Growth Properties of Stomach Submucosa

The ability of stomach submucosa to serve as an extracellular matrix to support in-vitro cell growth was tested by applying several cell types to the stomach submucosal tissue surface under standard cell culture conditions. The cell types tested included 3T3 fibroblasts, intestinal epithelium cells, and FR (fetal rat) mesenchymal cells. All three cell types showed the ability to proliferate readily upon this extracellular matrix without the addition of the supplements that would be needed to grow these cells on a plastic surface. Therefore, it can be concluded that the material contains necessary structure and composition "nutrients" to serve as a cell culture substrate for supporting cell growth.

EXAMPLE 3

Kirby-Bauer Test

To determine if stomach submucosa inhibits the growth of *H. pylori*, a Kirby-Bauer test was conducted. Individual colonies of *H. pylori* were isolated from a chocolate agar plate and used to inoculate a 1 ml. solution of sterile saline in a small tube. This sterile saline solution was then used to inoculate a chocolate agar plate through the use of a sterile cotton swab. A small piece of stomach submucosal tissue (approximately 25–50 mm. in diameter) was placed in the middle of the inoculated chocolate agar plate and pressed onto the surface of the plate to assure that the submucosa tissue sticks to the chocolate agar. The experiment was conducted in duplicate; two plates having the luminal side of the submucosa tissue in contact with the chocolate agar, and two plates having the abluminal surface of the submucosa tissue in contact with the agar. The plates were then incubated in a Campy jar in the 37° C. aerobic incubator for 3–4 days. After incubation the plates were removed from the incubator and Campy jar. The plates were observed to determine if there was a zone of inhibition surrounding the submucosal membranes. The Kirby-Bauer results show that stomach submucosal does not inhibit the growth of *H. pylori* or other organisms.

EXAMPLE 4

In-Vitro Growth of *H. pylori* on Stomach Submucosa Substrates

In a sterile hood, 2 mL of sterile saline was transferred to a small tube, and the saline was inoculated with *H. pylori* by swabbing 2 chocolate agar plates containing *H. pylori* and transferring the bacteria to the sterile saline. Chocolate agar is a commonly used rich agar medium comprising:

| | |
|---|---|
| Pancreatic digest of casein: | 7.5 g |
| Selected meat peptone: | 7.5 g |
| Corn starch | 1.0 g |
| Dipotassium phosphate | 4.0 g |
| Monopotassium phosphate | 1.0 g |
| Sodium chloride | 5.0 g |
| Agar | 12.0 g |
| Hemoglobin | 10.0 g |
| Iso Vitalex enrichment | 10. ml |

100 $\mu$l of the inoculated 2 ml saline solution was transferred into 5 mL of sterile saline for the McFarland test to determine cell concentration. $(5 \times 10^7)(5.1) = 0.1A$ and thus $A = 2.55 \times 10^9$ organisms/mL.

Serial dilutions of the *H. pylori*-containing saline solution were then prepared as follows: 300 $\mu$l from the inoculated 2 mL solution was added to 2700 $\mu$l of Walker's media giving a $10^{-1}$ concentration. Then, 300 $\mu$l of the $10^{-1}$ concentration solution was added to 2700 $\mu$l of Walker's media to give a $10^{-2}$ concentration. This method is continued until the $10^{-5}$ concentration is reached.

A sheet of stomach submucosa, having the luminal side up, was placed on the top of a lid from a 24 well tray. The lids of a separate sterile 24 well tray were marked with the labels of the appropriate controls and samples. The stomach submucosal tissue was cut into ~1 cm pieces using a scissors sterilized with alcohol and flamed, and the individual pieces were transferred into the appropriate marked wells using forceps sterilized with alcohol and flamed. Stomach submucosal tissue was placed into the wells either with the luminal side facing up or with the luminal side facing down. 400 ml of the appropriate concentration (dilution) of media plus bacteria ($10^{-3}$, $10^{-4}$, $10^{-5}$) was added to each of the wells. In addition, a series of "submucosa only control" wells were prepared, having only 400 µl of sterile saline added to the submucosal tissue containing wells. Finally, transfer media plus bacteria only (no submucosal tissue) was added to the appropriate wells as "bacteria only" controls.

The microliter tray was placed into a Campy® pouch and incubate for 24 hours at 37° C. in an aerobic ($O_2$) incubator. After incubation samples were taken from both the supernatant and the membrane of each of the microtiter wells and plated onto chocolate agar plates. Two samples were plated per concentration for dilutions up to $10^{-5}$ (including the original inoculated saline solution) to determine the growth efficiency of the *H. pylori* cultured in the presence of submucosal tissue.

To quantitate the number of bacteria present in the submucosal tissue supernatant, 100 µl of the supernatant was removed from the well, plated onto a chocolate agar plate and spread with an alcohol flamed hockey stick. To measure the number of *H. pylori* growing in and on the submucosal membrane, the cells were isolated from the tissue as follows: The submucosal tissue was removed from the well and cut into 2 or 3 pieces. These pieces were placed into a centrifuge tube containing 400 µl of fresh Walker's media and the tube was vortexed for 30 seconds. 100 µl of the vortexed solution was plated onto a chocolate agar plate and spread with an alcohol flamed hockey stick.

The inoculated chocolate agar plates were then incubated in a Campy® jar in a 37° C. aerobic incubator for 3–4 days. The plates were removed from the incubator and Campy® jar and number of colonies on each plate was determined by observation through a dissecting microscope. The number of organisms per mL was calculated: Number of colonies x the dilution factor (either $10^3$, $10^4$, or $10^5$)×10 (for the 100 µl placed on the plate)=The number of organisms per mL. For example 57 colonies on $10^{-3}$ dilution plate equals $57 \times 10^3 \times 10 = 5.7 \times 10^5$ organisms/mL. The accumulated data from the in vitro culture of *H. pylori* in the presence of stomach submucosa are indicated in Table 1.

TABLE 1

| Concentration | Sidedness | "In membrane" | "In supernatant" |
|---|---|---|---|
| $10^{-3}$ | Inner up A Plate A | To contaminated to count | Fungus, $3.16 \times 10^6$ |
| | Plate B | No Growth | Fungus, $2.49 \times 10^6$ |
| | Inner up B Plate A | $2.0 \times 10^5$ | Contaminated, $1.38 \times 10^6$ |
| | Plate B | Fungus, $1.3 \times 10^5$ | Contaminated, TCTC |
| | Outer up A Plate A | Contaminated, Fungus, $2.4 \times 10^5$ | Contaminated, No Growth |
| | Plate B | Contaminated, $2.1 \times 10^5$ | Contaminated, TCTC |
| | Outer up B Plate A | Fungus, $1.7 \times 10^5$ | $3.21 \times 10^6$ |

TABLE 1-continued

| Concentration | Sidedness | "In membrane" | "In supernatant" |
|---|---|---|---|
| | Plate B | Fungus, $2.2 \times 10^5$ | Fungus $3.22 \times 10^6$ |
| $10^{-4}$ | Inner up A Plate A | $4.0 \times 10^5$ | Contaminated, $6.3 \times 10^6$ |
| | Plate B | $2.0 \times 10^5$ | Contaminated, $2.5 \times 10^6$ |
| | Inner up B Plate A | $3.0 \times 10^5$ | Contaminated, $1.7 \times 10^6$ |
| | Plate B | $2.0 \times 10^5$ | $2.5 \times 10^6$ |
| | Outer up A Plate A | Contaminated, NG | Contaminated, NG |
| | Plate B | Contaminated, $2.0 \times 10^5$ | Contaminated, NG |
| | Outer up B Plate A | Contaminated, Fungus, $2.0 \times 10^5$ | $4.2 \times 10^6$ |
| | Plate B | Contaminated, $2.7 \times 10^6$ | $4.3 \times 10^6$ |
| $10^{-5}$ | Inner up A Plate A | No Growth | $7.0 \times 10^6$ |
| | Plate B | No Growth | $2.0 \times 10^6$ |
| | Inner up B Plate A | Fungus, No Growth | $3.0 \times 10^6$ |
| | Plate B | Fungus, No Growth | $6.0 \times 10^6$ |
| | Outer up A Plate A | Fungus, No Growth | Contaminated, No Growth |
| | Plate B | Fungus, No Growth | $2.0 \times 10^6$ |
| | Outer up B Plate A | No Growth | Contaminated, $4.0 \times 10^6$ |
| | Plate B | No Growth | $2.0 \times 10^6$ |

Results

The calculated values were compared to the numbers obtained from the original serial dilutions and the McFarland standard to determine the extent of the proliferation that occurred during the incubation of *H. pylori* in the presence of the stomach submucosal tissue. As the data of Table 1 indicates, stomach submucosa tissue is capable of supporting *H. pylori* growth. The number of colonies present on the chocolate agar plates increased with each serial dilution as expected which indicates growth of *H. pylori*. Contamination continues to be a problem in these experiments. Accordingly, the optimal conditions for growing *H. pylori* on stomach submucosa have not yet been determined. However the experiments demonstrate stomach submucosa's ability to support *H. pylori* growth. It is anticipated that once the optimal conditions have been defined the difficulties with contamination by other organisms will be eliminated.

The present experiment analyzed the growth of *H. pylori* on stomach submucosal tissue substrates in the presence of bacterial cell culture media. In an alternative embodiment, the stomach submucosal tissue substrates can be used to culture *H. pylori* in the presence of eukaryotic cell culture media. The presence of the eukaryotic cell culture media, and most preferably mammalian cell culture media, will provide a more physiological environment and thus optimize the function of the stomach submucosal tissue as a host for microbial residence and pathogenicity.

Once the conditions have been optimized for growing *H. pylori* in vitro, the antibiotic sensitivity of these organisms can be evaluated in an environment that more closely mimics the natural habitat of these organisms. Therefore the culture substrates of the present invention can be used not only for detecting the presence of *H. pylori* from a source tissue, but can also be utilized to investigate the optimal antibiotics and antibiotic concentrations necessary to effectively treat patients infected with *H. pylori*.

What is claimed is:

1. A method for identifying and diagnosing prokaryotic infectious agents, said method comprising the steps of obtaining a sample from a source wherein said sample contains prokaryotic infectious agents, inoculating a cell growth substrate comprising submucosal tissue of a warm-blooded vertebrate with the sample wherein the submucosal tissue is delaminated from muscle layers and from the luminal portion of tunica mucosa, culturing the sample on said substrate under conditions conducive to the proliferation of said prokaryotic infectious agents, and identifying and diagnosing the prokaryotic infectious agents.

2. The method of claim 1 wherein the sample is taken from a vertebrate species.

3. A method for analyzing, in vitro, the growth characteristics of prokaryotic infectious agents, said method comprising the steps of inoculating a cell growth substrate comprising submucosal tissue of a warm-blooded vertebrate with the prokaryotic infectious agent wherein the submucosal tissue is delaminated from muscle layers and from the luminal portion of tunica mucosa, culturing the prokaryotic infectious agent on said substrate under a selected variable cell growth condition, and histologically examining the prokaryotic infectious agent inoculated on said substrate.

* * * * *